United States Patent
Zhang et al.

(10) Patent No.: US 10,267,753 B2
(45) Date of Patent: Apr. 23, 2019

(54) MULTI-ENERGY SPECTRUM X-RAY GRATING-BASED IMAGING SYSTEM AND IMAGING METHOD

(71) Applicant: Nuctech Company Limited, Beijing (CN)

(72) Inventors: Li Zhang, Beijing (CN); Zhiqiang Chen, Beijing (CN); Xiaolei Jiang, Beijing (CN); Xiaohua Zhu, Beijing (CN); Xin Jin, Beijing (CN)

(73) Assignee: Nutech Company Limited, Beijing (CN)

( * ) Notice: Subject to any disclaimer, the term of this patent is extended or adjusted under 35 U.S.C. 154(b) by 120 days.

(21) Appl. No.: 15/328,881

(22) PCT Filed: Oct. 28, 2015

(86) PCT No.: PCT/CN2015/093090
§ 371 (c)(1),
(2) Date: Jan. 24, 2017

(87) PCT Pub. No.: WO2016/070739
PCT Pub. Date: May 12, 2016

(65) Prior Publication Data
US 2017/0234811 A1    Aug. 17, 2017

(30) Foreign Application Priority Data
Nov. 4, 2014   (CN) .......................... 2014 1 0610841

(51) Int. Cl.
*G01N 23/04*    (2018.01)
*G01N 23/046*   (2018.01)
(Continued)

(52) U.S. Cl.
CPC ......... *G01N 23/046* (2013.01); *A61B 6/4241* (2013.01); *A61B 6/4291* (2013.01);
(Continued)

(58) Field of Classification Search
CPC .... G01N 23/04; G01N 23/046; G01N 23/087; G01N 2223/408; G01N 2223/401;
(Continued)

(56) References Cited

U.S. PATENT DOCUMENTS 8,139,711 B2    3/2012  Takahashi
2009/0086883 A1   4/2009  Härer et al.
(Continued)

FOREIGN PATENT DOCUMENTS

CN    101396272 A    4/2009
CN    101532969 A    9/2009
(Continued)

OTHER PUBLICATIONS

Hao, Jia et al., "Multi-energy X-ray Imaging Technique and its Application in Computed Tomography,"; CT Theory and Applications Mar. 2011, vol. 20, No. 1, pp. 141-150; 10 pgs.
(Continued)

*Primary Examiner* — Jurie Yun
(74) *Attorney, Agent, or Firm* — Knobbe Martens Olson & Bear LLP

(57) ABSTRACT

The present disclosure relates to a multi-spectrum X-ray grating-based imaging system and imaging method. In one illustrative implementation, an exemplary multi-spectrum X-ray grating-based imaging system according to the present disclosure may comprise an incoherent X-ray source for emitting X-rays to irradiate an object to be detected, a grating module comprising a first absorption grating and a second absorption grating which are disposed in parallel to each other and are sequentially arranged in an X-ray propagation direction, and an energy-resolved detecting device for receiving the X-rays that have passed through the first absorption grating and the second absorption grating.

20 Claims, 6 Drawing Sheets

(51) Int. Cl.
*G01N 23/087* (2018.01)
*A61B 6/00* (2006.01)
*A61B 6/03* (2006.01)

(52) U.S. Cl.
CPC .............. *A61B 6/482* (2013.01); *A61B 6/484* (2013.01); *G01N 23/087* (2013.01); *A61B 6/032* (2013.01); *A61B 6/4035* (2013.01); *A61B 6/463* (2013.01); *G01N 2223/401* (2013.01); *G01N 2223/408* (2013.01); *G01N 2223/419* (2013.01); *G01N 2223/605* (2013.01)

(58) Field of Classification Search
CPC ........ G01N 2223/419; G01N 2223/605; A61B 6/4241; A61B 6/482; A61B 6/03; A61B 6/032; A61B 6/035; A61B 6/4035; A61B 6/405; A61B 6/4291
USPC ............................................. 378/5, 62, 98.8
See application file for complete search history.

(56) References Cited

U.S. PATENT DOCUMENTS

| | | | |
|---|---|---|---|
| 2010/0246764 | A1 | 9/2010 | Itoh et al. |
| 2011/0293064 | A1 | 12/2011 | Huang et al. |
| 2012/0281217 | A1 | 11/2012 | Ouchi et al. |
| 2013/0094625 | A1 | 4/2013 | Huang et al. |
| 2014/0185746 | A1 | 7/2014 | Baturin et al. |
| 2014/0226783 | A1 | 8/2014 | Ning et al. |

FOREIGN PATENT DOCUMENTS

| | | | |
|---|---|---|---|
| CN | 101726503 | A | 6/2010 |
| CN | 101943668 | A | 1/2011 |
| CN | 102047344 | A | 5/2011 |
| CN | 102221565 | A | 10/2011 |
| CN | 105120755 | A | 12/2015 |
| EP | 2060909 | B1 | 9/2011 |
| JP | 2011 153969 | A | 8/2011 |
| WO | WO 2012/073710 | | 11/2011 |
| WO | WO 2012/073710 | A1 | 6/2012 |

OTHER PUBLICATIONS

International Search Report and Written Opinion received in Application No. PCT/CN2015/093090 dated Feb. 5, 2016 (12 pgs), and English translation of ISR (2 pgs); 14 pages total.

Extended European Search Report dated Jun. 30, 2017, received in related EP Application No. 15839132.6, 7 pages.

Hao J, Zhang L, Chen ZQ, et al. Multi-energy X-ray Imaging Technique and Its Application in Computed Tomography[J].CT Theory and Applications, 2011, 20(1): 141-150.

Office Action in Chinese Patent Application No. 201410610841.4, dated Jul. 24, 2018.

Office Action in Chinese Patent Application No. 201410610841.4, dated Nov. 30, 2017.

MULTI-ENERGY SPECTRUM X-RAY GRATING-BASED IMAGING SYSTEM AND IMAGING METHOD

CROSS-REFERENCE TO RELATED APPLICATIONS

This application is U.S. 371 National Phase of and claims priority to PCT Application No. PCT/CN2015/093090, filed on Oct. 28, 2015, published as WO2016/070739, entitled "MULTI-ENERGY SPECTRUM X-RAY GRATING-BASED IMAGING SYSTEM AND IMAGING METHOD", and which claim benefit/priority to Chinese Patent Application No. 201410610841.4, filed on Nov. 4, 2014, published as CN105628718A, which are incorporated herein by reference in their entirety.

TECHNICAL FIELD

The present disclosure generally relates to an X-ray grating-based imaging technique, and more particularly, to a multi-spectrum X-ray grating-based imaging system and imaging method.

BACKGROUND

In modern society, X-ray has been widely used, for example in CT scanning apparatus, for scanning and imaging many objects. Generally, conventional X-ray scanning and imaging technique uses X-ray attenuation through materials to nondestructively detect interiors of objects. The more different in density of internal components of the object are, the greater will be the effect of the conventional X-ray imaging technique. Substances consisting of light elements have weak absorbing abilities for X-ray, thus conventional X-ray imaging technique can hardly identify their internal structures. In this case, other auxiliary means, such as injecting contrast agent into biological tissues, do not help to obtain clear images, without which a lot of inconveniences may be caused. In the 1990s, there appeared an X-ray phase-contrast imaging technique which uses information concerning the phase shift of an X-ray beam to observe changes in density of electrons in an object, thereby determining the inner structure of the object. Generally, the early phase-contrast imaging methods use interference or diffraction of coherent or partially coherent X-rays to improve the low-contrast resolution of the radiation image. On such a basis, in the patent applications CN101532969A entitled "System and method for X-ray grating-based phase-contrast imaging" (Patent Reference 1) and CN101726503A entitled "X-ray phase contrast tomography imaging" (Patent Reference 2), wherein all the contents of said patent applications are incorporated into the present application by reference, HUANG Zhifeng et al. put forward a novel technical concept for incoherent grating-based phase-contrast imaging. Specifically, the said references use two absorption gratings which can translate relative to each other for several steps within a range of one grating period, and a detecting device acquires one image for each translation step; after the image acquisition process for one grating period has been finished, for each pixel, the sample intensity curve and the background intensity curve are compared such that the information concerning the refraction image of the object to be detected can be calculated. This approach has a good phase-contrast imaging effect. Said approach can be performed with multicolored and incoherent X-ray sources and thus can be embodied as simple and easy devices.

Furthermore, during the progress of the X-ray imaging technology, there also appeared a dark-field imaging technique. Said dark-field imaging technique uses indirect light such as scattered light, diffracted light, refracted light, fluorescent light and the like to illuminate objects, and then form images of the internal structures of the objects by means of the difference in their capabilities of scattering X-rays. Generally, the dark-field imaging with hard X-rays is difficult to well perform, since the special optical properties of hard X-rays make it is difficult to manufacture optical components required for dark-field imaging with hard X-rays. However, the dark-field imaging with hard X-rays has a better capability to identify and detect the internal microstructures of objects than the bright-field imaging and the phase-contrast imaging. Since the scattering of the hard X-rays is at a micrometer level or a nanometer level, the dark-field imaging with hard X-rays can be used to identify the internal ultrafine structures of objects, which, in contrast, cannot be determined by the bright-field imaging and phase-contrast imaging with hard X-rays. In 2009, in the patent application CN101943668A entitled "X-ray dark-field imaging system and method" (Patent Reference 3), wherein all the contents of said patent application are incorporated into the present application by reference, HUANG Zhifeng et al. put forward a technical solution that performs dark-field imaging of objects by using X-rays. Specifically, the technical solution of the said reference comprises: emitting X-rays to an object to be detected; enabling one of two absorption gratings to perform stepping within at least one period; for each step, the detecting device receiving and converting X-rays into an electrical signal; after stepping over at least one period, representing the X-ray intensity at each pixel of the detecting device as an intensity curve; comparing, at each pixel of the detecting device, the intensity curve with the object to be detected and the intensity curve without the object, and calculating the second moment of the scattering angle distribution at each pixel; taking images of the object from different angles, and then obtaining a scattering information image of the object according to a CT reconstruction algorithm.

The above-mentioned grating-based imaging techniques require the stepping process to obtain the intensity curve at each detection unit (pixel) of the detecting device. The basic principle of the stepping technique is: after a source grating is fixed adjacent to an X-ray source, in the technique based on a Talbot-Lau interference method, a phase grating or resolution grating is relatively translated for several steps within a range of one grating period; while in the technique based on a classic optical method, two absorption gratings are translated relative to each other for several steps in a range of one grating period. The detecting device acquires one image for each translation step. After finishing the image acquisition process for one grating period, for each pixel, the sample intensity curve and the background intensity curve are compared such that the refraction image information, attenuation image information and dark-field image information can be calculated. Generally, conventional stepping technique comprises translating the phase gratings, the resolution gratings or the absorption gratings. In 2010, in the patent application CN102221565A entitled "X-ray source grating-stepping imaging system and imaging method" (Patent Reference 4), wherein all the contents of said patent application are incorporated into the present application by reference, HUANG Zhifeng et al. put forward a grating stepping method for an X-ray source. Specifically, since the source grating has a period of dozens of micrometers, the above approach requires a substantially lower stepping accuracy as compared to the conventional stepping methods.

All the aforementioned grating-based imaging techniques adopt conventional energy-deposition X-ray detecting devices. For X-rays having board energy spectrums generated from common X-ray sources (for example, common X-ray machine, distributed X-ray source, X-ray accelerator and the like), the conventional energy-deposition X-ray detecting device can only acquire a weighted average energy response for scanned objects, which may result in radiation hardening and cannot effectively determine the composition of the objects.

SUMMARY

On the basis of existing techniques such as X-ray grating-based phase-contrast imaging, dark-field imaging and X-ray source-grating-stepping imaging system, the present disclosure provides a multi-spectrum X-ray grating-based imaging system and imaging method achieved in an incoherent manner, which adopt an energy-resolved detecting device to detect X-rays having different energies in an energy range of broad X-ray spectrum from common X-ray source (the X-ray energy ranges from 0 to a preset value of outputting beam energy). The embodiments of the present application can solve problems such as spectrum hardening, image objects in different energy ranges, obtain information concerning energy dimension, and effectively identify component of objects.

According to an aspect of the present disclosure, there is provided a multi-spectrum X-ray grating-based imaging system, comprising:

an incoherent X-ray source, for emitting X-rays to irradiate an object to be detected;

a grating module, comprising a first absorption grating and a second absorption grating which are disposed in parallel to each other and are sequentially arranged in an X-ray propagation direction; and an energy-resolved detecting device, for receiving the X-rays that have passed through the first absorption grating and the second absorption grating.

Furthermore, in the multi-spectrum X-ray grating-based imaging system according to the embodiment of the present disclosure, the grating module is configured such that one of the first absorption grating and the second absorption grating performs phase stepping actions within at least one period. During each phase stepping action, the incoherent X-ray source emits X-rays to irradiate the object to be detected, and the energy-resolved detecting device receives the X-rays and performs spectrum identification of the received X-rays. After a series of phase stepping actions and data acquisitions over a period, at each pixel on the energy-resolved detecting device, X-ray intensities in each energy range are represented as an intensity curve.

The present disclosure innovatively combines spectrum-identifiable X-ray detection technique with grating-based imaging technique. The present disclosure gives full play to superiorities of grating-based imaging technique. For example, three kinds of information (i.e., attenuation, phase-contrast and dark-field) that indicates internal structure of object may be simultaneously obtained during one scanning process such that internal structural information and composition information of object can be more fully revealed. Furthermore, the present disclosure can incorporate the multi-spectrum analysis technique to avoid disadvantageous of existing imaging procedures, take advantage of more information from multi-spectrum to achieve identification of substance components, and has great application values in various fields such as medical imaging, security checking and the like.

The present disclosure can eliminate adverse effects of broad spectrum X-ray source on the grating-based imaging technique, solve inherent problems such as radiation hardening, substantially improve signal-to-noise ratio of image, and achieve identification of substance components. As compared to conventional X-ray imaging techniques, the present disclosure can achieve high contrast imaging of weak-absorbing substances (for example, mammary gland, soft tissues such as blood vessel and muscle, fiber material, insects and the like). As compared to existing grating-based imaging techniques, the present disclosure can substantially improve signal-to-noise ratio of image, solve problem of radiation hardening, and achieve identification of substance components by using variations of linear attenuation coefficient, phase factor, generalized scattering coefficient of scanned sample as a function of X-ray energy. The present disclosure develops novel concepts and approaches for applying the phase-contrast imaging technique into various fields such as medical, biology and industrial materials, and has great practical significance and application value.

Furthermore, the multi-spectrum X-ray grating-based imaging system according to the embodiment of the present disclosure further comprises: a source grating, disposed at a position between the incoherent X-ray source and the object to be detected and adjacent to the incoherent X-ray source, wherein the source grating is able to move in a direction parallel to the first absorption grating and the second absorption grating. The grating module is configured such that the first absorption grating and the second absorption grating are fixed, while the source grating is configured to perform stepping actions in at least one period. During each phase stepping action, the incoherent X-ray source emits X-rays to irradiate the object to be detected, and the energy-resolved detecting device receives the X-rays and performs spectrum identification of the received X-rays. After a series of phase stepping actions and data acquisitions over a period, at each pixel on the energy-resolved detecting device, X-ray intensities in each energy range are represented as an intensity curve.

Furthermore, the multi-spectrum X-ray grating-based imaging system according to the embodiment of the present disclosure further comprises: an actuation device for enabling the object to be detected to rotate by an angle relative to the entire multi-spectrum X-ray grating-based imaging system.

Furthermore, in the multi-spectrum X-ray grating-based imaging system according to the embodiment of the present disclosure, at each rotation angle, a series of phase stepping actions are repeated over a period, and then an image of the object to be detected is reconstructed according to a predetermined CT image reconstruction algorithm.

Furthermore, in the multi-spectrum X-ray grating-based imaging system according to the embodiment of the present disclosure, the multi-spectrum X-ray grating-based imaging system comprises a computer workstation, which comprises: a data processing module, for processing data information and calculating pixel values at respective spots on the object to be detected; an image reconstruction module, for reconstructing an image of the object to be detected based on the calculated pixel values; and a control module, for controlling the incoherent X-ray source, the grating module and the energy-resolved detecting device.

Furthermore, in the multi-spectrum X-ray grating-based imaging system according to the embodiment of the present disclosure, the computer workstation comprises: a display unit for displaying the image of the object to be detected.

Furthermore, in the multi-spectrum X-ray grating-based imaging system according to the embodiment of the present disclosure, the computer workstation is able to calculate refraction information of X-rays at a predetermined spot on the object to be detected by comparing an intensity curve with the presence of the object to be detected to a background intensity curve in the absence of the object to be detected, and thus calculate corresponding pixel value.

Furthermore, in the multi-spectrum X-ray grating-based imaging system according to the embodiment of the present disclosure, the computer workstation is able to calculate scattering information of X-rays at a predetermined spot on the object to be detected by comparing an intensity curve with the presence of the object to be detected to a background intensity curve in the absence of the object to be detected, and thus calculate corresponding pixel value.

Furthermore, in the multi-spectrum X-ray grating-based imaging system according to the embodiment of the present disclosure, the computer workstation is able to calculate attenuation information of X-rays at a predetermined spot on the object to be detected by comparing an intensity curve with the presence of the object to be detected to a background intensity curve in the absence of the object to be detected, and thus calculate corresponding pixel value.

Furthermore, according to an aspect of the present disclosure, there is provided an X-ray grating-based imaging method, comprising the following steps:

enabling one of a first absorption grating and a second absorption grating which are parallel to each other and are sequentially arranged in an X-ray propagation direction to perform phase stepping actions within at least one period, wherein during each phase stepping action, an incoherent X-ray source emits X-rays to irradiate an object to be detected, and an energy-resolved detecting device receives the X-rays that have passed through the first absorption grating and the second absorption grating and performs spectrum identification of the received X-rays;

after a series of phase stepping actions and data acquisitions over a period, at each pixel on the energy-resolved detecting device, representing X-ray intensities in each energy range as an intensity curve;

calculating pixel values at each pixel by comparing an intensity curve at each pixel on the energy-resolved detecting device to an intensity curve in the absence of the object to be detected; and obtaining image information of the object to be detected according to the pixel values.

Furthermore, in the X-ray grating-based imaging method according to the embodiment of the present disclosure, the object to be detected is rotated, wherein at each rotation angle, the phase stepping actions are repeated, and an image of the object to be detected is reconstructed according to a predetermined CT image reconstruction algorithm.

Furthermore, in the X-ray grating-based imaging method according to the embodiment of the present disclosure, refraction information of X-rays at a predetermined spot on the object to be detected is calculated by comparing an intensity curve with the presence of the object to be detected to a background intensity curve in the absence of the object to be detected, and thus corresponding pixel value is calculated.

Furthermore, in the X-ray grating-based imaging method according to the embodiment of the present disclosure, scattering information of X-rays at a predetermined spot on the object to be detected is calculated by comparing an intensity curve with the presence of the object to be detected to a background intensity curve in the absence of the object to be detected, and thus corresponding pixel value is calculated.

Furthermore, in the X-ray grating-based imaging method according to the embodiment of the present disclosure, attenuation information of X-rays at a predetermined spot on the object to be detected is calculated by comparing an intensity curve with the presence of the object to be detected to a background intensity curve in the absence of the object to be detected, and thus corresponding pixel value is calculated.

According to the present disclosure, the multi-spectrum X-ray grating-based imaging system according to the present disclosure is achieved in an incoherent manner. The present disclosure employs a multi-spectrum X-ray grating-based imaging system to achieve a detection of different energy ranges of broad spectrum X-rays generated from common X-ray source (the X-ray energy ranges from 0 to a preset value of outputting beam energy). The present disclosure maintains original advantages of grating-based imaging techniques (for example, three kinds of information (i.e., attenuation, phase-contrast and dark-field) may be obtained during one imaging process), and can also solves problems of existing grating-based imaging techniques (including radiation hardening and other problems). Moreover, the present disclosure avoids disadvantages resulted from multi-spectrum in imaging by an energy-deposition detecting device, and exploits advantages of imaging by spectrum-identifiable detecting device. The present disclosure takes advantage of more information from the multi-spectrum to achieve identification of substance components, and has great application values in various fields such as medical imaging, security detection and the like.

DETAILED DESCRIPTION

Below, the present disclosure will be described in details by reference to the appended drawings.

Figure 1:
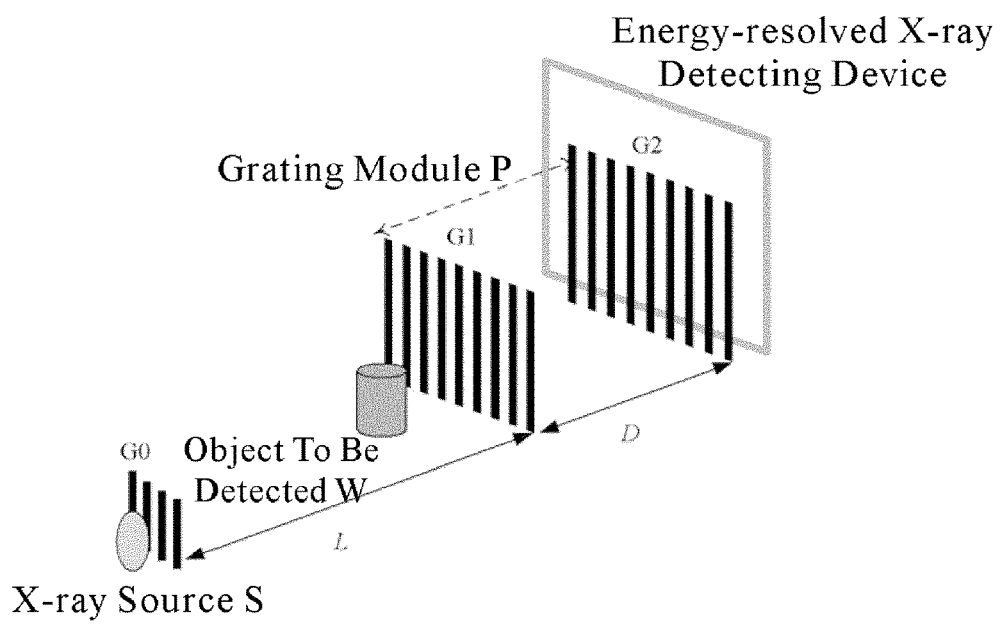
FIG. 1 is a schematic diagram of a multi-spectrum X-ray grating-based imaging system according to an embodiment of the disclosure.

FIG. 1 is a schematic diagram of a multi-spectrum X-ray grating-based imaging system according to an embodiment of the disclosure. The multi-spectrum X-ray grating-based imaging system according to the present disclosure is able to image and detect objects. As shown in FIG. 1, a multi-spectrum X-ray grating-based imaging system according to an exemplary embodiment of the disclosure comprises: an X-ray source S, a grating module P and an energy-resolved detecting device. The X-ray source S is adapted to emit X-ray beams (for example, broad-spectrum X-rays) towards an object to be detected (i.e., an object to be scanned W as shown in FIG. 1). Optionally, when the X-ray source has a large focus spot, a collimator comprising plural slits (i.e., a source grating G0) can be provided to generate a group of small-focus-spot linear sources which will emit X-ray beams towards the object to be scanned. As shown in FIG. 1, with the source grating G0 provided, the source grating G0 is disposed at a position between the X-ray source S and the object to be detected and adjacent to the X-ray source S. The grating module P comprises a first absorption grating G1 and a second absorption grating G2. The two absorption gratings G1 and G2 are parallel to each other and are sequentially arranged in an X-ray propagation direction. In operation, X-rays refracted and scattered by the object to be detected pass through the first absorption grating G1 and the second absorption grating G2, thereby forming an X-ray signal with varying intensities. The energy-resolved detecting device is adapted to receive the above X-ray signal with varying intensity (for example, broad-spectrum X-rays) and transform the X-ray signal into an electrical signal, thereby achieving an identification of X-ray energies and obtaining information under multiple energies. Moreover, according to an embodiment of the present disclosure, the X-ray source S may be an incoherent X-ray source.

Figure 2:
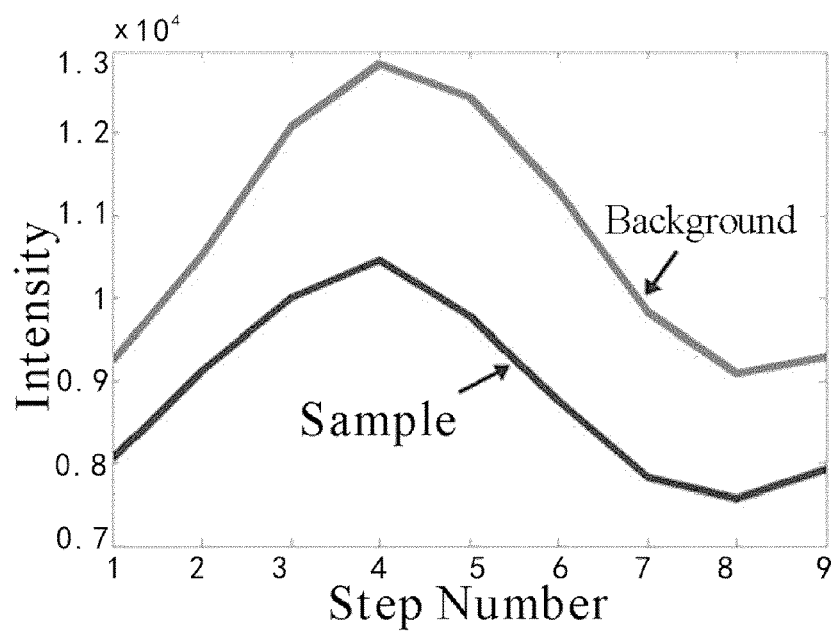
FIG. 2 is a schematic diagram of an intensity curve obtained in a stepping scan process according to an embodiment of the disclosure.

Furthermore, in the imaging and detecting process, the object to be detected (i.e., an object to be scanned W as shown in FIG. 1) is disposed between the X-ray source S and the first absorption grating G1. Optionally, with the source grating G0 provided, the object to be detected is disposed between the source grating G0 and the first absorption grating G1. Furthermore, the multi-spectrum X-ray grating-based imaging system according to the present disclosure may further comprise a computer workstation. The computer workstation controls the X-ray source, the grating module and the energy-resolved detecting device to implement the following process: the grating module performs a phase stepping process (i.e., the first absorption grating G1 and the second absorption grating G2 perform a phase stepping process); for each step, the X-ray source emits X-rays; and the energy-resolved detecting device receives the X-rays and converts the received X-rays into an electrical signal and performs a spectrum identification of the X-rays. After a series of phase stepping actions (i.e., a period of phase stepping process) and data acquisitions, at each pixel of the energy-resolved detecting device, the intensities of X-rays in each energy range may be represented as an intensity curve (as shown in FIG. 2, which shows an intensity curve at a certain energy range). The intensity curve at each pixel spot on the energy-resolved detecting device is compared to an intensity curve in the absence of the object to be detected (the intensity curve in the absence of the object to be detected is known). The pixel value at each pixel spot is calculated from a variation of the intensity curves. Therefore, three kinds of information (i.e., attenuation image, phase-contrast image and dark-field image) that can reflect structural information of the object are obtained. Furthermore, the present disclosure can perform the phase stepping action of the grating module P in the same way with the prior art (for example, Patent Documents 1-3). Furthermore, the phase stepping action with the source grating G0 may also be performed in the same way with the prior art (for example, Paten Document 4). For example, the first absorption grating G1 and the second absorption grating G2 may be fixed, while the source grating G0 performs the stepping actions in at least one period; during each phase stepping action, the X-ray source S emits X-rays to irradiate the object to be detected; the energy-resolved detecting device receives the X-rays and identifies the spectrums of the received X-rays; and after a series of phase stepping actions and data acquisitions over a period, at each pixel on the energy-resolved detecting device, the X-ray intensities in each energy range may be represented as an intensity curve.

Furthermore, in the present disclosure, the first absorption grating G1 and the second absorption grating G2 may be parallel to each other with a distance D therebetween, and there may be a distance L between the X-ray source S and the grating G1.

Furthermore, the periods of the first absorption grating G1 and the second absorption grating G2 are preferably between 0.1 and 30 μm. The absorbing material of the gratings is heavy metal (such as gold (Au)). For example, the height of the gold absorbing material is determined by the applied X-ray energy, and is generally between 10 and 100 μm. For example, for X-rays of 20 keV, gold with a height of more than 16 μm can block 90% of the X-rays.

As stated above, the detecting device used in the present disclosure is an energy-resolved detecting device, which is able to receive broad spectrum X-rays (polychromatic X-ray) with varying intensities, convert the X-ray signal into an electrical signal, resolve intensity variation of X-rays with different energies and obtain information under multiple energies. The present disclosure may use the same method with the prior art to perform identification of broad spectrum X-rays. However, the present disclosure is not limited to this. The present disclosure may also use other types of X-ray detecting devices so long as they can achieve the above function.

Furthermore, in the multi-spectrum X-ray grating-based imaging system according to the present disclosure, all of the control of the entire imaging system, data transmission, image reconstruction and data processing can be accomplished by the computer workstation. The scanning control information, position information, projection data and the like are input into the computer workstation via a data acquisition system. The computer workstation performs extraction of many kinds of information of the object, data preprocessing and image reconstruction, and then displays them on a display.

Furthermore, the computer workstation may comprise a data processing module. The data processing module is configured to: calculate variation in the intensity (curve) after the X-ray passes through the object to be detected according to digitally processable electrical signals output from the energy-resolved detecting device; calculate the absorption information, scattering information or refraction information at a certain point on the object to be detected with respect to the X-ray according to the variation in said intensity (curve); and calculate the pixel information concerning the object to be detected by use of the aforementioned information. These functions can also be achieved by programmed software, or alternatively achieved by a dedicated hardware chipset.

Furthermore, the computer workstation may further comprise a control module (not shown in FIG. 1) for controlling the operations (such as relative rotation, X-ray emission and information acquisition) of the X-ray source S, the object to be detected W, the first and second absorption gratings G1 and G2, the energy-resolved detecting device and the like. Preferably, the control module and the data processing module can be integrated together and implemented by a single general or dedicated processor.

Furthermore, the computer workstation may further comprise an imaging module (not shown in FIG. 1) for reconstructing an image of the object to be detected according to the obtained pixel information, outputting and displaying the image. Moreover, the imaging module may be implemented by the processor that also serves as the data processing module.

Furthermore, the multi-spectrum X-ray grating-based imaging system according to the disclosure may further comprise an actuation device for enabling the object to be detected to rotate by an angle relative to the entire multi-spectrum X-ray grating-based imaging system under the control of the computer workstation. The phase stepping process is repeated at each rotation angle, and thus pixel values for X-ray imaging may be obtained at multiple angles. Then, a stereo image of the object to be detected is reconstructed according to a predetermined CT image reconstruction algorithm. The actuation device has a structure for achieving a relative rotating of the object to be detected.

Furthermore, the computer workstation may comprise a display unit for displaying the reconstructed image. The display unit can be implemented by a general display.

Figure 3:
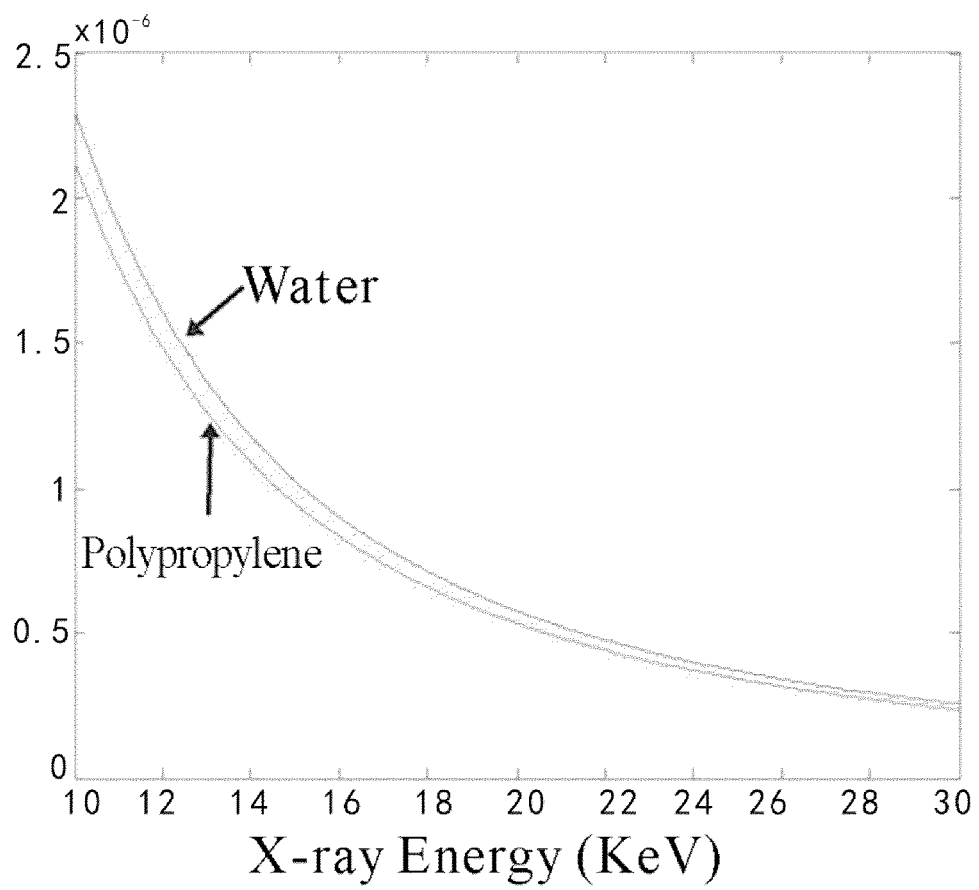
FIG. 3 is a schematic diagram which illustrates a relation between a phase factor of an interaction of water with X-rays and X-ray energy, and a relation between a phase factor of an interaction of polypropylene with X-rays and X-ray energy, respectively.
Figure 4:
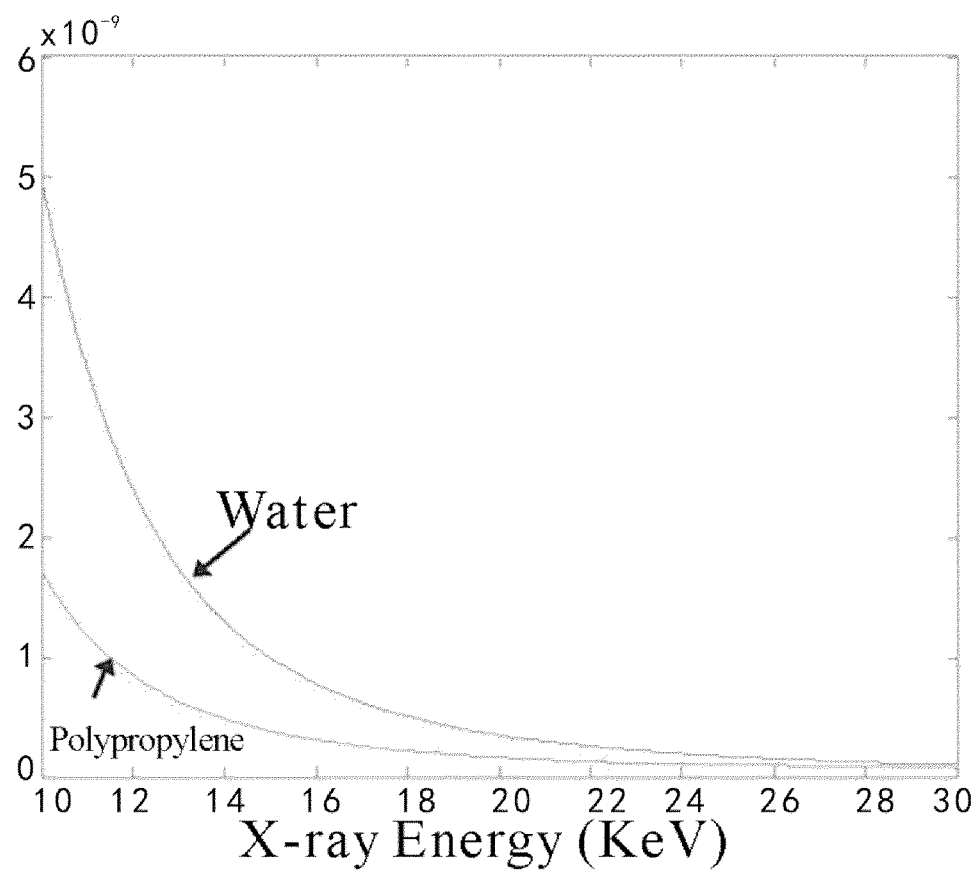
FIG. 4 is a schematic diagram which illustrates a relation between an absorption factor of an interaction of water with X-rays and X-ray energy, and a relation between an absorption factor of an interaction of polypropylene with X-rays and X-ray energy, respectively.

Below, the significance of spectrum identification may be understood from the perspective of interaction of X-rays with substance. The interaction of X-rays with a substance may be represented by a complex refractive index n of the substance with respect to X-rays. The complex refractive index n is defined by the following expression (1):

$$n = 1 - \delta - i\beta \quad (1)$$

wherein, δ denotes phase factor which is related to phase shift cross section of the substance; and β denotes absorption factor which is related to linear attenuation coefficient of the substance with respect to rays. The symbols δ and β used herein are both related to X-ray energy. For example, FIG. 3 and FIG. 4 show curves indicating relations of phase factors and absorption factors of either of water and polypropylene with X-ray energy, respectively. FIG. 3 shows a relation between a phase factor of an interaction of water with X-rays and X-ray energy, and a relation between a phase factor of an interaction of polypropylene with X-rays and X-ray energy, respectively. FIG. 4 shows a relation between an absorption factor of an interaction of water with X-rays and X-ray energy, and a relation between an absorption factor of an interaction of polypropylene with X-rays and X-ray energy, respectively. As can be seen from FIG. 3 and FIG. 4, the phase factors and the absorption factors decrease as X-ray energy increases. Conventional energy-deposition X-ray detecting device cannot show such correlation with energy, but acquires average values in broad spectrum, which may also lead to the problem of X-ray spectrum hardening and may further influence the imaging effect. The energy-resolved detecting device can achieve identification of X-ray energy, can acquire phase factor and absorption factor for corresponding energy, and thus can obtain more accurate values and better image quality and can prevent spectrum hardening and other problems.

Figure 5:
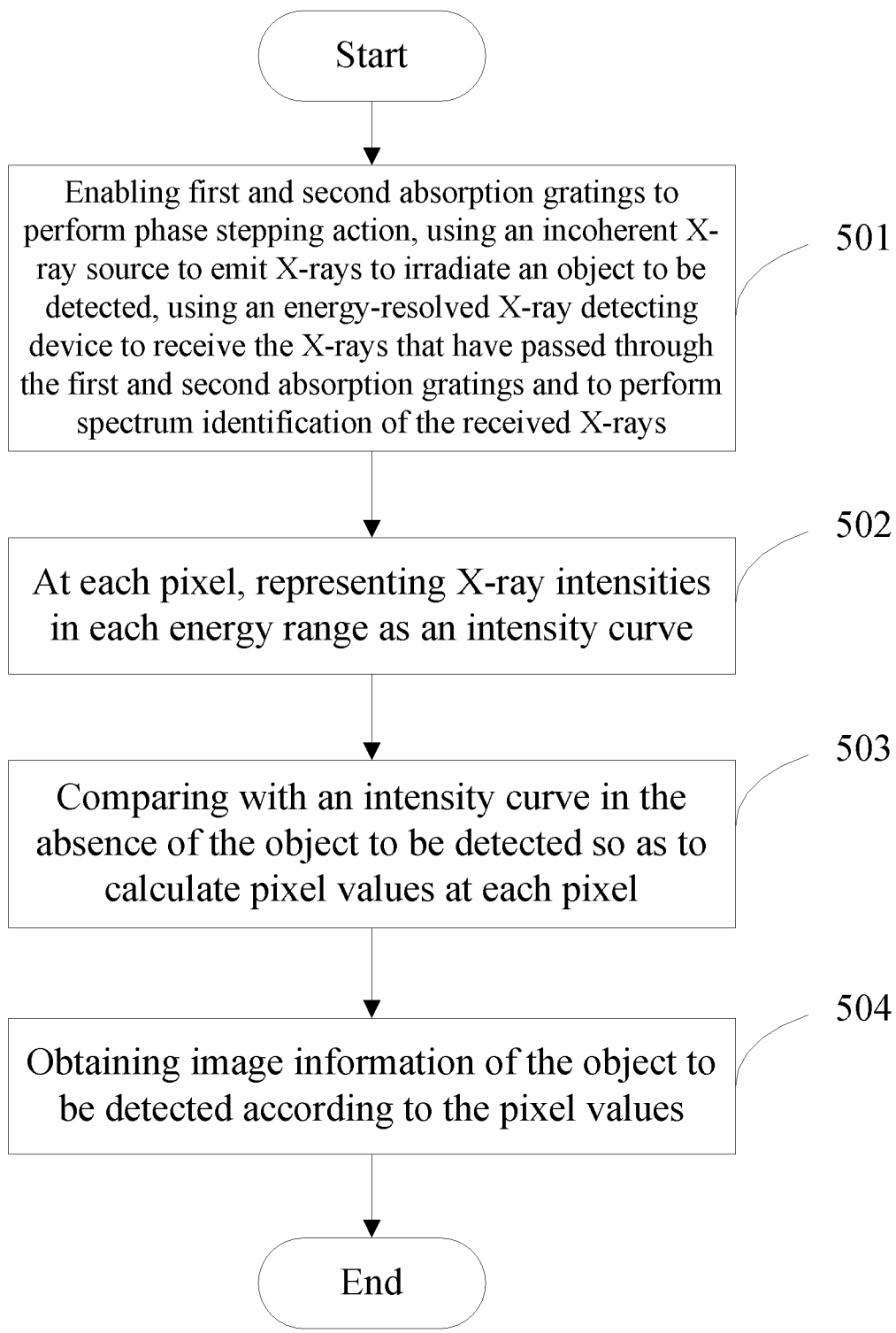
FIG. 5 is a flow chart of a method for imaging and detecting an object by using X-rays, according to an embodiment of the disclosure.

FIG. 5 shows a flow chart of a method for imaging and detecting an object by using X-rays according to an embodiment of the disclosure. As shown in FIG. 5, the method for imaging and detecting an object by using X-rays according to an embodiment of the present disclosure comprises the following steps: at Step 501, enabling one of a first absorption grating and a second absorption grating to perform phase stepping action within at least one period, wherein during each phase stepping action, an incoherent X-ray source emits X-rays to irradiate an object to be detected, and an energy-resolved detecting device receives the X-rays that have passed through the first absorption grating G1 and the second absorption grating G2 and convert them into an electrical signal, thereby achieving spectrum identification of the received X-rays. At Step 502, after a series of phase stepping actions and data acquisitions over a period, at each pixel on the energy-resolved detecting device, X-ray intensities in each energy range are represented as an intensity curve. At Step 503, the intensity curve at each pixel on the energy-resolved detecting device is compared to an intensity curve in the absence of the object to be detected, so as to calculate the pixel values at each pixel. At Step 504, image information of the object to be detected is obtained according to the calculated pixel values. Furthermore, an image of the object to be detected can be reconstructed from the obtained image information. Moreover, when a source grating G0 is provided, the first absorption grating G1 and the second absorption grating G2 may be fixed, while the source grating G0 performs the stepping actions within at least one period; during each phase stepping action, the X-ray source S emits X-rays to irradiate the object to be detected; the energy-resolved detecting device receives the X-rays and performs spectrum identification of the received X-rays; after a series of phase stepping actions and data acquisitions over a period, at each pixel on the energy-resolved detecting device, the X-ray intensities in each energy range are represented as an intensity curve; and then the image of the object to be detected is obtained as described above.

The present disclosure can be applied to a CT imaging system. According to an aspect of the present disclosure, there is provided a multi-spectrum X-ray grating-based CT imaging system, which comprises, in addition to the multi-spectrum X-ray grating-based imaging system according to an embodiment of the present disclosure, a rotating device. The rotating device is adapted to relatively rotate the object to be detected with respect to the X-ray source, gratings, X-ray detecting device and the like. This relative rotation may be the case of rotating the object while keeping other parts stationary, or the case of keeping the object stationary while rotating the X-ray source, the gratings, the X-ray detecting device and the like together. In a CT mode, the multi-spectrum X-ray grating-based CT imaging system can obtain refraction angle information, small-angle scattering information and corresponding planar pixel information at various projection angles, and then reconstruct cross-section images of the interior of the object by use of predetermined algorithms.

The present disclosure can eliminate adverse effects of broad spectrum X-ray source on the grating-based imaging technique, solve inherent problems such as radiation hardening, substantially improve signal-to-noise ratio of image, and achieve identification of substance components. As compared to conventional X-ray imaging techniques, the present disclosure can achieve high contrast imaging of weak-absorbing substances (for example, mammary gland, soft tissues such as blood vessel and muscle, fiber material, insects and the like). As compared to existing grating-based imaging techniques, the present disclosure can substantially improve signal-to-noise ratio of image, solve problem of radiation hardening, and achieve identification of substance components by using variations of linear attenuation coefficient, phase factor, generalized scattering coefficient of scanned sample as a function of X-ray energy. The present disclosure develops novel concepts and approaches for applying the phase-contrast imaging technique into various fields such as medical, biology and industrial materials, and has great practical significance and application value.

APPLICATION EXAMPLES

Below, several application examples of the present disclosure will be described.

Figure 6:
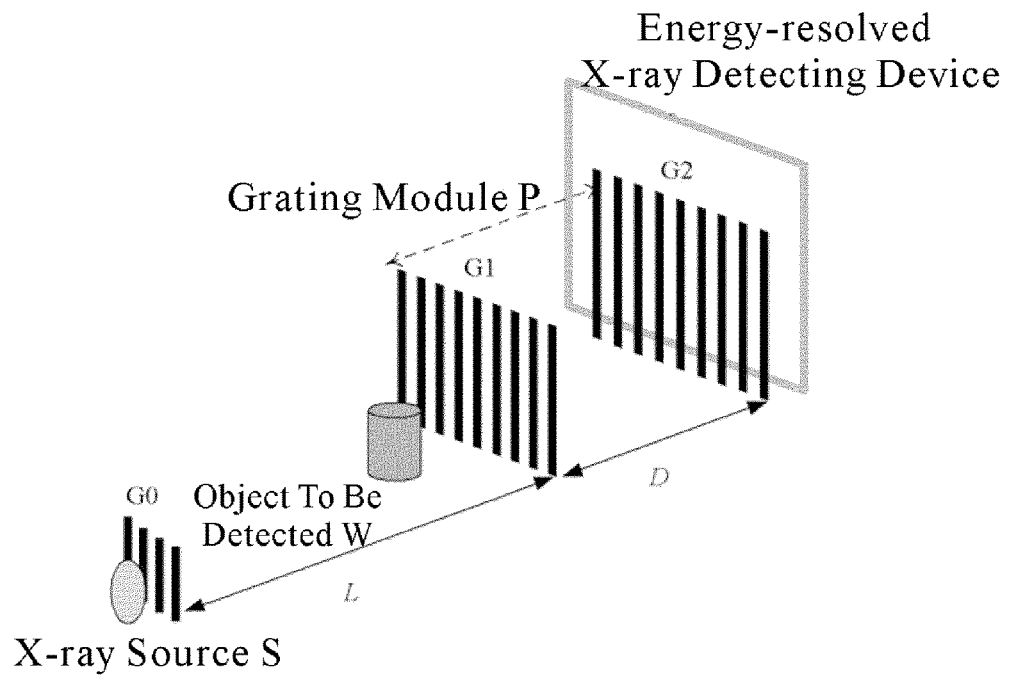
FIG. 6 is a schematic diagram of an application example of the disclosure.

FIG. 6 is a schematic diagram of a first application example of the disclosure. As shown in FIG. 6, the first application example shows a case where the multi-spectrum X-ray grating-based imaging system according to the embodiment of the present disclosure is applied into X-ray photography. The multi-spectrum X-ray grating-based imaging system can simultaneously acquire three kinds of images (i.e., attenuation, phase-contrast and dark-field) during one scanning process, and thus can be applied into new-generation mammary machine and the like. Furthermore, as shown in FIG. 6, the source grating G0 shown in the drawing is optional. That is to say, the source grating G0 may be provided or not in this case.

Figure 7:
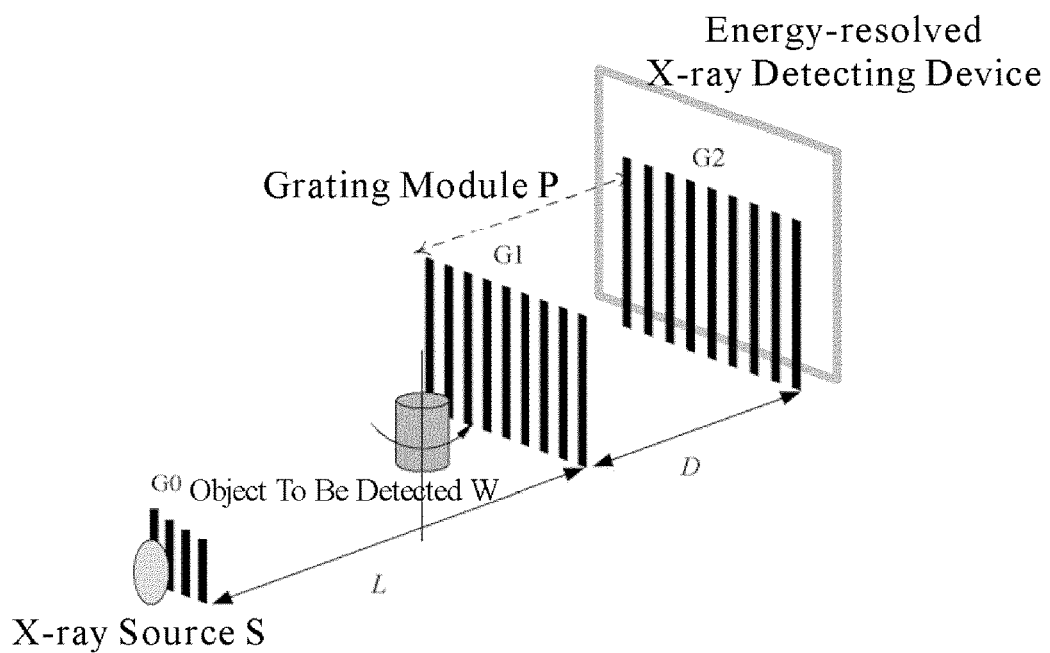
FIG. 7 is a schematic diagram of another application example of the disclosure.

Furthermore, FIG. 7 is a schematic diagram of a second application example of the disclosure. As shown in FIG. 7, the second application example shows a case where the multi-spectrum X-ray grating-based imaging system according to the embodiment of the present disclosure is applied into X-ray CT imaging. The sample to be scanned (i.e., an object to be scanned W in FIG. 7) can be rotated around a direction perpendicular to a light path. Therefore, three-dimensional information concerning substance structure can be obtained, and substance identification can be performed based on spectrum information. Similarly, as shown in FIG. 7, the source grating G0 shown in the drawing is optional. That is to say, the source grating G0 may be provided or not in this case.

Figure 8:
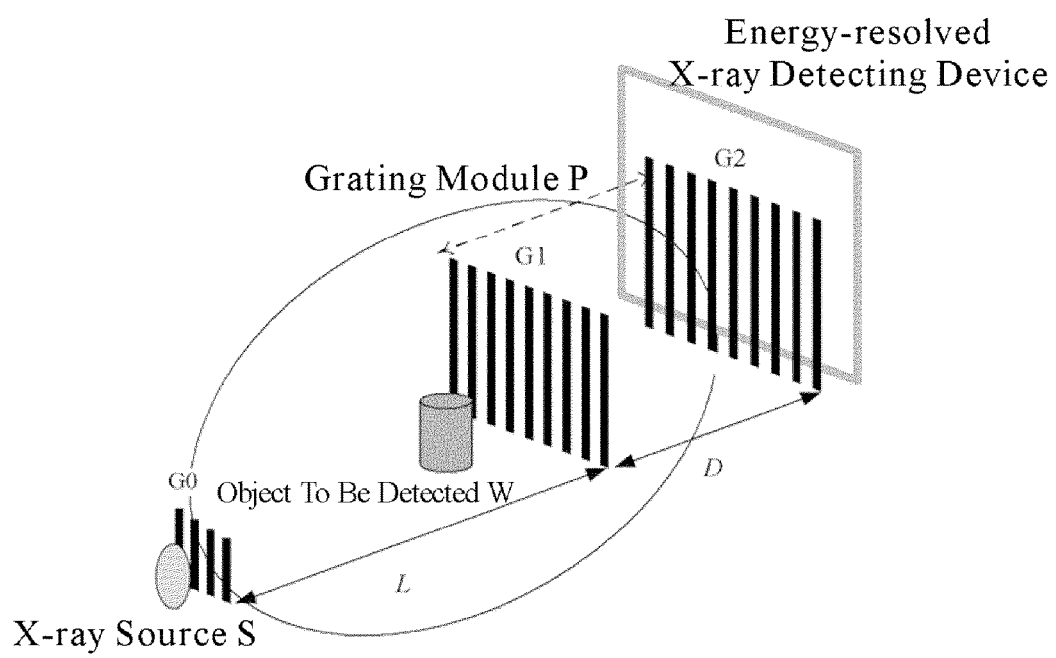
FIG. 8 is a schematic diagram of another application example of the disclosure.

Furthermore, FIG. 8 is a schematic diagram of a third application example of the disclosure. As shown in FIG. 8, the third application example shows a case where the multi-spectrum X-ray grating-based imaging system according to the embodiment of the present disclosure is applied into X-ray CT imaging. The mechanical structure of the entire multi-spectrum X-ray grating-based imaging system can be rotated around a direction perpendicular to a light path. Therefore, three-dimensional information concerning substance structure can be obtained, and substance identification can be performed based on spectrum information. Similarly, as shown in FIG. 8, the source grating G0 shown in the drawing is optional. That is to say, the source grating G0 may be provided or not in this case.

As stated above, the multi-spectrum X-ray grating-based imaging system according to the present disclosure is achieved in an incoherent manner (i.e., the present disclosure adopts an incoherent X-ray source). The present disclosure employs a multi-spectrum X-ray grating-based imaging system to achieve a detection of different energy ranges of broad spectrum X-rays generated from common X-ray source (the X-ray energy ranges from 0 to a preset value of outputting beam energy). The present disclosure maintains original advantages of grating-based imaging techniques (for example, three kinds of information (i.e., attenuation, phase-contrast and dark-field) may be obtained during one imaging process), and can also solves problems of existing grating-based imaging techniques (including radiation hardening and other problems). Moreover, the present disclosure avoids disadvantages resulted from multi-spectrum in imaging by an energy-deposition detecting device, and exploits advantages of imaging by spectrum-identifiable detecting device. The present disclosure takes advantage of more information from the multi-spectrum to achieve identification of substance components, and has great application values in various fields such as medical imaging, security detection and the like.

The present disclosure innovatively combines spectrum-identifiable X-ray detection technique with grating-based imaging technique. The present disclosure gives full play to superiorities of grating-based imaging technique. For example, three kinds of information (i.e., attenuation, phase-contrast and dark-field) that indicates internal structure of object may be simultaneously obtained during one scanning process such that internal structural information and composition information of object can be more fully revealed. Furthermore, the present disclosure can incorporate the multi-spectrum analysis technique to avoid disadvantageous of existing imaging procedures, take advantage of more information from multi-spectrum to achieve identification of substance components, and has great application values in various fields such as medical imaging, security detection and the like.

It should be understood that the disclosure is not limited to the precise structure as described above and shown in the figures, but can have various modification and alternations without departing from the scope of the disclosure.

What is claimed is:

1. A multi-spectrum X-ray grating-based imaging system, comprising:
    an incoherent X-ray source, for emitting X-rays to irradiate an object to be detected;
    a grating module, comprising a first absorption grating and a second absorption grating which are disposed in parallel to each other and are sequentially arranged in an X-ray propagation direction; and
    an energy-resolved detecting device, for receiving the X-rays that have passed through the first absorption grating and the second absorption grating,
        wherein the grating module is configured such that one of the first absorption grating and the second absorption grating performs phase stepping actions within at least one period,
        wherein during each phase stepping action, the incoherent X-ray source emits X-rays to radiate the object to be detected, and the energy-resolved detecting device receives the X-rays and performs spectrum identification of the received X-rays, and
        wherein after a series of phase stepping actions and data acquisitions over a period, at each pixel on the energy-resolved detecting device, X-ray intensities in each energy range are represented as an intensity curve.

2. The multi-spectrum X-ray grating-based imaging system according to claim 1, further comprising:
    an actuation device for enabling the object to be detected to rotate by an angle relative to the entire multi-spectrum X-ray grating-based imaging system.

3. The multi-spectrum X-ray grating-based imaging system according to claim 2, wherein at each rotation angle, a series of phase stepping actions are repeated over a period, and then an image of the object to be detected is reconstructed according to a predetermined CT image reconstruction algorithm.

4. The multi-spectrum X-ray grating-based imaging system according to claim 1, wherein the multi-spectrum X-ray grating-based imaging system comprises a computer workstation, and wherein the computer workstation comprises:
- a data processing module, for processing data information and calculating pixel values at respective spots on the object to be detected;
- an image reconstruction module, for reconstructing an image of the object to be detected based on the calculated pixel values; and
- a control module, for controlling the incoherent X-ray source, the grating module and the energy-resolved detecting device.

5. The multi-spectrum X-ray grating-based imaging system according to claim 4, wherein the computer workstation comprises:
- a display unit for displaying the image of the object to be detected.

6. The multi-spectrum X-ray grating-based imaging system according to claim 4, wherein the computer workstation is configured to calculate refraction information of X-rays at a predetermined spot on the object to be detected by comparing an intensity curve with the presence of the object to be detected to a background intensity curve in the absence of the object to be detected, and thus calculate corresponding pixel value.

7. The multi-spectrum X-ray grating-based imaging system according to claim 4, wherein the computer workstation is configured to calculate scattering information of X-rays at a predetermined spot on the object to be detected by comparing an intensity curve with the presence of the object to be detected to a background intensity curve in the absence of the object to be detected, and thus calculate corresponding pixel value.

8. The multi-spectrum X-ray grating-based imaging system according to claim 4, wherein the computer workstation is configured to calculate attenuation information of X-rays at a predetermined spot on the object to be detected by comparing an intensity curve with the presence of the object to be detected to a background intensity curve in the absence of the object to be detected, and thus calculate corresponding pixel value.

9. The multi-spectrum X-ray grating-based imaging system according to claim 4, wherein the computer workstation is configured to calculate refraction information, scattering information and attenuation information of X-rays at a predetermined spot on the object to be detected by comparing an intensity curve with the presence of the object to be detected to a background intensity curve in the absence of the object to be detected, and thus calculate corresponding pixel value.

10. The multi-spectrum X-ray grating-based imaging system according to claim 1, wherein the periods of the first absorption grating and the second absorption grating are between 0.1 and 30 μm.

11. A multi-spectrum X-ray grating-based imaging system, comprising:
- an incoherent X-ray source, for emitting X-rays to irradiate an object to be detected;
- a grating module, comprising a first absorption grating and a second absorption grating which are disposed in parallel to each other and are sequentially arranged in an X-ray propagation direction;
- an energy-resolved detecting device, for receiving the X-rays that have passed through the first absorption grating and the second absorption grating, and
- a source grating, disposed at a position between the incoherent X-ray source and the object to be detected and adjacent to the incoherent X-ray source, wherein the source grating is configured to move in a direction parallel to the first absorption grating and the second absorption grating, wherein the grating module is configured such that the first absorption grating and the second absorption grating are fixed, while the source grating is configured to perform phase stepping actions in at least one period, wherein during each phase stepping action, the incoherent X-ray source emits X-rays to irradiate the object to be detected, and the energy-resolved detecting device receives the X-rays and performs spectrum identification of the received X-rays, and wherein after a series of phase stepping actions and data acquisitions over a period, at each pixel on the energy-resolved detecting device, X-ray intensities in each energy range are represented as an intensity curve.

12. The multi-spectrum X-ray grating-based imaging system according to claim 11, further comprising:
- an actuation device for enabling the object to be detected to rotate by an angle relative to the entire multi-spectrum X-ray grating-based imaging system.

13. The multi-spectrum X-ray grating-based imaging system according to claim 12, wherein at each rotation angle, a series of phase stepping actions are repeated over a period, and then an image of the object to be detected is reconstructed according to a predetermined CT image reconstruction algorithm.

14. The multi-spectrum X-ray grating-based imaging system according to claim 11, wherein the multi-spectrum X-ray grating-based imaging system comprises a computer workstation, and
wherein the computer workstation comprises:
- a data processing module, for processing data information and calculating pixel values at respective spots on the object to be detected;
- an image reconstruction module, for reconstructing an image of the object to be detected based on the calculated pixel values; and
- a control module, for controlling the incoherent X-ray source, the grating module and the energy-resolved detecting device.

15. An X-ray grating-based imaging method, comprising:
- enabling one of a first absorption grating and a second absorption grating which are parallel to each other and are sequentially arranged in an X-ray propagation direction to perform phase stepping actions within at least one period, wherein during each phase stepping action, an incoherent X-ray source emits X-rays to irradiate an object to be detected, and an energy-resolved detecting device receives the X-rays that have passed through the first absorption grating and the second absorption grating and performs spectrum identification of the received X-rays;
- after a series of phase stepping actions and data acquisitions over a period, representing X-ray intensities in each energy range, at each pixel on the energy-resolved detecting device, as an intensity curve;
- calculating pixel values at each pixel by comparing an intensity curve at each pixel on the energy-resolved detecting device to an intensity curve in the absence of the object to be detected; and
- obtaining image information of the object to be detected according to the pixel values.

16. The X-ray grating-based imaging method according to claim 15, further comprising:
- rotating the object to be detected, wherein at each rotation angle, the phase stepping actions are repeated, and reconstructing an image of the object to be detected according to a predetermined CT image reconstruction algorithm.

17. The X-ray grating-based imaging method according to claim 15, further comprising calculating refraction information of X-rays at a predetermined spot on the object to be detected by comparing the intensity curve with the presence of the object to be detected to a background intensity curve in the absence of the object to be detected, and thus calculating corresponding pixel value.

18. The X-ray grating-based imaging method according to claim 15, further comprising calculating scattering information of X-rays at a predetermined spot on the object to be detected by comparing the intensity curve with the presence of the object to be detected to a background intensity curve in the absence of the object to be detected, and thus calculating corresponding pixel value.

19. The X-ray grating-based imaging method according to claim 15, further comprising calculating attenuation information of X-rays at a predetermined spot on the object to be detected by comparing the intensity curve with the presence of the object to be detected to a background intensity curve in the absence of the object to be detected, and thus calculating corresponding pixel value.

20. The X-ray grating-based imaging method according to claim 15, further comprising calculating refraction information, scattering information and attenuation information of X-rays at a predetermined spot on the object to be detected by comparing the intensity curve with the presence of the object to be detected to a background intensity curve in the absence of the object to be detected, and thus calculating corresponding pixel value.

* * * * *